United States Patent [19]

Flaherty

[11] Patent Number: 5,728,267
[45] Date of Patent: Mar. 17, 1998

[54] CONCENTRATOR FOR SEPARATING SMALL SAMPLES IN A CENTRIFUGE

[76] Inventor: James E. Flaherty, 23152 Verdugo Dr., Laguna Hills, Calif. 92653

[21] Appl. No.: 340,059

[22] Filed: Nov. 15, 1994

(Under 37 CFR 1.47)

[51] Int. Cl.⁶ .................................................. B01D 63/00
[52] U.S. Cl. ........................... 210/321.67; 210/321.75; 210/321.84; 210/360.1; 210/380.1; 210/329; 210/473; 422/101
[58] Field of Search ............................ 210/321.84, 380.1, 210/369, 407, 329, 781, 360.1, 978, 473, 321.67, 321.75; 454/36; 422/101

[56] References Cited

U.S. PATENT DOCUMENTS

| | | | |
|---|---|---|---|
| 4,632,761 | 12/1986 | Bowers et al. | 210/781 |
| 4,755,301 | 7/1988 | Bowers et al. | 210/650 |
| 4,829,005 | 5/1989 | Friedman et al. | 210/321.84 |
| 4,832,851 | 5/1989 | Bowers et al. | 210/321.84 |

*Primary Examiner*—Ana Fortuna
*Attorney, Agent, or Firm*—Edgar W. Averill, Jr.

[57] ABSTRACT

A concentrator for concentrating a sample solution including molecules in solution which are larger than their molecular weight cutoff of a membrane in the concentrator. The concentrator has a sample reservoir which includes a bottom floor having an annular central wall surrounding a central opening. A membrane is held on a membrane support member positioned below the sample reservoir and a filtrate vial is held below the membrane to collect liquid which is passed through the membrane. A retentate vial is held over the top of the reservoir and after the sample has been concentrated the filtrate vial is removed and the remaining part of the assembly inverted. The assembly is then replaced in the centrifuge and spun to transfer the concentrated sample into the retentate vial. The membrane support member is made from spokes with open spaces between the spokes.

7 Claims, 2 Drawing Sheets

CONCENTRATOR FOR SEPARATING SMALL SAMPLES IN A CENTRIFUGE

BACKGROUND OF THE INVENTION

The field of the invention is the concentration of macro molecules using a filter or a membrane which has pores through which the macro molecules will not pass. Such concentrators are known and a problem exists when the solution is concentrated to essentially dryness and the macro molecules are then difficult to recover from a upper surface of the membrane.

One solution to this problem is shown in U.S. Pat. Nos. 4,632,761 and 4,755,301. As shown best in FIG. 4b of the drawings of those patents, the assembly must be placed in a "fixed angle centrifuge". If the sample is placed in a centrifuge having swing buckets the sample will be concentrated essentially to dryness with the above-referred problems.

SUMMARY OF THE INVENTION

It is an object of the present invention to provide a concentrator which will not concentrate a sample to dryness either in a fixed angle centrifuge or a centrifuge with swing buckets.

The present invention is for a concentrator for concentrating a sample solution including molecules in solution which are larger than the molecular weight cutoff of a membrane. The concentrator includes a sample reservoir having a cylindrical side wall, an open top and a bottom which has a bottom floor. A central wall surrounds a central opening in the bottom floor and a space is provided between the inner wall of the cylindrical side wall and the central wall on the bottom floor of the sample reservoir. A membrane support member is held below the bottom of the sample reservoir and has support webs with open space between the support webs. A membrane is held on the membrane support webs and a generally cylindrical filtrate vial is held below the membrane support member. A retentate vial is held over the open top of the sample reservoir and after the sample has been concentrated and the filtrate has passed into the filtrate vial, the filtrate vial is removed. The remaining assembly is then inverted and returned to the centrifuge and again spun and the concentrated sample passes from the concentrated sample well into the retentate vial. Preferably both the retentate vial and the filtrate vial have exterior threads near the top opening thereof and caps are provided to help retain the sample and the filtrate after the concentration step.

DESCRIPTION OF THE PREFERRED EMBODIMENTS

Figure 1:
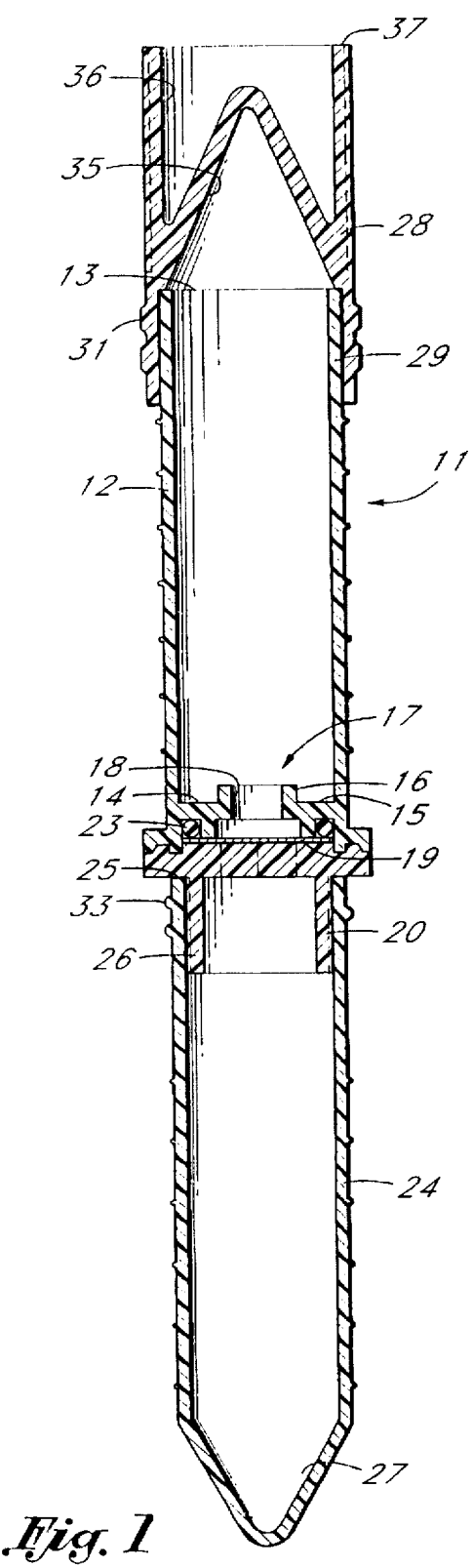
FIG. 1 is a cross-sectional side view of the concentrator of the present invention.
Figure 2:
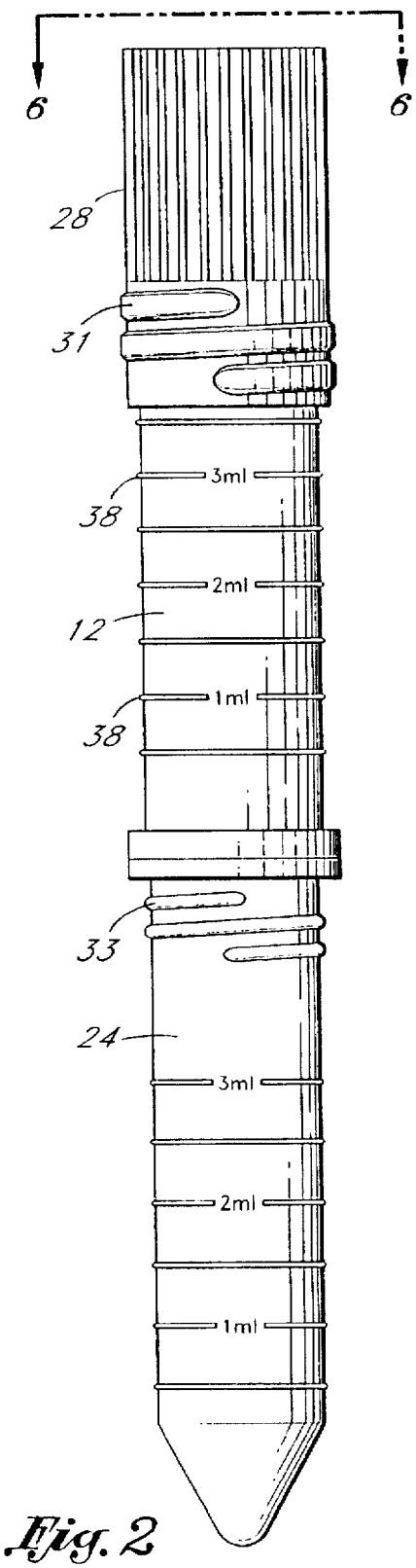
FIG. 2 is an exterior side view thereof.

The concentrator of the present invention is shown in FIG. 1 and indicated generally by reference character 10. Concentrator 10 has a sample reservoir 11 which has a cylindrical side wall 12, an open top 13 and a bottom 14. The bottom 14 has a bottom floor 15 and a central wall 16. The central wall has a crest 17 and a central opening 18.

Figure 3:
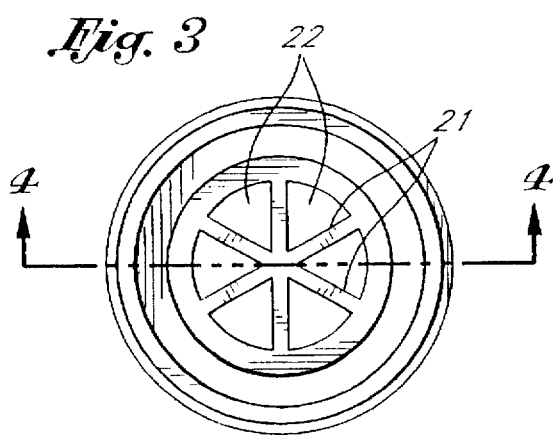
FIG. 3 is an enlarged top view of the membrane support member of the concentrator of FIG. 1.
Figure 4:
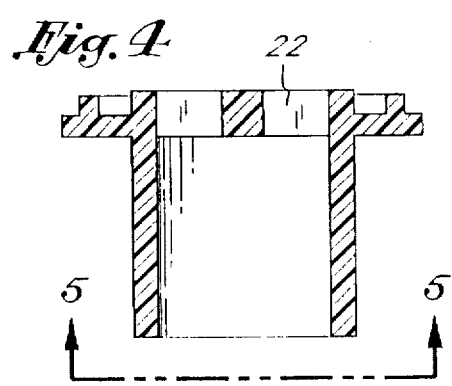
FIG. 4 is a cross-sectional view taken along line 4—4 of FIG. 3.
Figure 5:
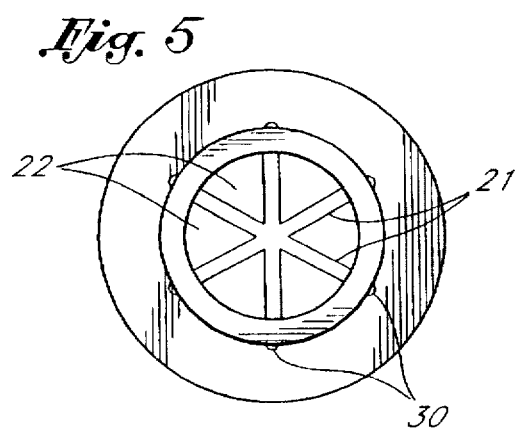
FIG. 5 is a bottom view of the membrane support member of FIG. 3.

A membrane 19 is held on a membrane support member 20 which is shown best in FIGS. 3, 4 and 5. The membrane 19 rests on the spokes 21 shown in FIGS. 3 and 5 and the space between spokes 21 is completely open. The open space is indicated by reference character 22 in FIGS. 3, 4 and 5.

Membrane 19 is held in a leak proof manner against bottom 14 of sample reservoir 11 by an O-ring 23.

A filtrate vial 24 is also generally cylindrical in shape and has an open top 25 into which fits a downwardly depending skirt 26 of membrane support member 20 is inserted. The bottom of filtrate vial 24 is generally conical as indicated at reference character 27.

A retentate vial 28 is placed over the open top 13 of sample reservoir 11. Venting of the space within sample reservoir 11 is provided by a plurality of ribs formed vertically along the outer surface of sample reservoir 11 and the position of the ribs is indicated by reference character 29. Similar ribs 30 are placed along the outer surface of downwardly depending skirt 26 so that air may pass out of filtrate vial 24 as filtrate passes into it (see FIG. 5).

Figure 7:
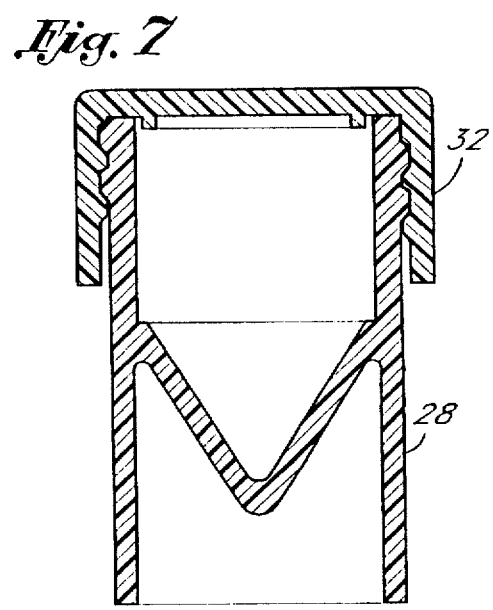
FIG. 7 is a cross-sectional side view of the retentate vial of the concentrator of FIG. 1, further including a cap.

The outer surface of retentate vial 28 includes a plurality of threads 31 which mate with the inner threads on cap 32 shown in FIG. 7. This permits the concentrated sample to be sealed after the concentration steps are complete. Similarly, outer threads 33 are formed on the outer surface of filtrate vial 24 near the open top 25 thereof so that a cap may also be placed over the open top in the event the filtrate is to be saved.

Figure 6:
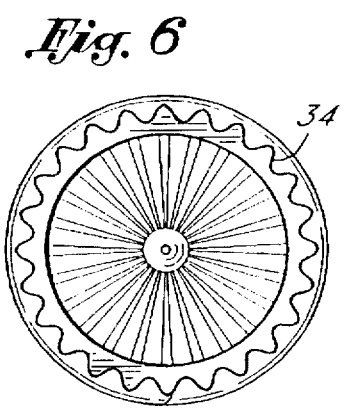
FIG. 6 is a top view of the concentrator of FIG. 1.

Preferably the outer surface of retentate vial 28 is knurled as indicated by reference character 34 in FIG. 6 to facilitate both the removal of the vial from sample reservoir 11 as well as facilitating the tightening of cap 32 thereon. Preferably retentate vial 28 has a generally conical floor 35 and a cylindrical wall 36 terminating in a bottom edge 37 which provides a support surface as shown best in FIG. 7 of the drawings.

In use the device is assembled as shown in FIG. 1 except that retentate vial 28 has not yet been placed thereon. A sample to be concentrated is poured in through open top 13 after which retentate vial 28 is placed thereon. The assembly as shown in FIG. 1 is then placed in a centrifuge which may be either a fixed axis centrifuge or a centrifuge with swing buckets. The assembly is spun forcing that portion of the sample which has molecules smaller than the cutoff of membrane 19 to pass into filtrate vial 24. A certain amount of the sample, however, is not permitted to pass through membrane 19 since it is retained against bottom floor 15 below the crest 17 of central wall 16. In the event the centrifuge is a fixed axis centrifuge this amount will be held at an angle with respect bottom floor 15 and if used in a centrifuge with swing buckets will be held straight across crest 17. After the centrifuge is stopped filtrate vial 24 is removed and capped if desired and the remaining assembly is inverted and replaced into the centrifuge. It is then again spun and the concentrated sample passes into the retentate vial 28 after which the assembly is removed and the retentate vial separated from sample reservoir 11 and capped as shown in FIG. 7.

The assembly of the present invention permits the rapid and easily reproduced concentration of a sample. Preferably marking indicia 38 are provided on the outer surface of sample reservoir 11 so that a measured amount of sample may easily be added. The volume of concentrated sample will also always be the same because the volume surrounding central wall 16 is fixed. Thus, it is not necessary to carefully monitor the amount of time the sample is spun since it will be safely retained around central wall 16.

The device of the present invention utilizing relatively thin spokes with open space 22 therebetween provides a large space for passage of filtrate through the membrane. This increases the speed with which the concentration can be carried out as most of the surface of membrane 19 is available for passage of filtrate.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A concentrator for concentrating a sample solution including molecules in solution which are larger than the molecular weight cutoff of a membrane in the concentrator, said concentrator comprising:

a sample reservoir having a cylindrical side wall, an open top and a bottom including a bottom floor having a lower surface and an upper surface terminating in a central wall surrounding a central opening, said central wall having an annular crest parallel to said bottom floor and the volume below said annular crest and above said bottom floor being a concentrated sample well;

a membrane support member held below said bottom of said sample reservoir, said membrane support including a membrane support web positioned below said central opening in the bottom of said sample reservoir;

a membrane held on said membrane support web, said membrane held in a leak proof manner by membrane sealing means so that any liquid on the top of said membrane cannot pass around said membrane;

a generally cylindrical filtrate vial having an open top, a closed bottom, said filtrate vial being held by said membrane support member and positioned below said membrane so that filtrate passing through said membrane will be collected in said filtrate vial; and a retentate vial held over the open top of said sample reservoir whereby a sample to be concentrated may be placed in said sample reservoir and the filtrate vial may be removed and the rest of the assembly may be placed in a centrifuge and spun so that the molecules in the sample which are smaller than the cutoff of the membrane will pass through the membrane but a small volume of concentrated sample will be held in the concentrated sample well after which the assembly may be inverted and spun again forcing the concentrated sample into the retentate vial.

2. The concentrator of claim 1 wherein the membrane support web comprises a plurality of spokes and said spokes form three equally spaced diametric bars with an open space between said bars.

3. The concentrator of claim 1 wherein said retentate vial has a generally conical floor surrounded by a cylindrical wall with a bottom edge which extends past said generally conical floor.

4. The concentrator of claim 3 wherein said cylindrical wall of the retentate vial has an outer surface and the outer surface of said cylindrical is serrated;

wherein the outer surface of the cylindrical wall of the retentate vial is threaded and the assembly further includes a cap with threads which may be screwed onto the retentate vial.

5. A concentrator for concentrating a sample solution including molecules in solution which are larger than the molecular weight cutoff of a membrane in the concentrator, said concentrator comprising:

a sample reservoir having a cylindrical side wall with a central axis, an open top and a bottom including a bottom floor having a lower surface and an upper surface terminating in a circular central wall concentrically located with respect to the central axis of said cylindrical side wall of said sample reservoir, said central wall surrounding a central opening, said central wall having an annular crest parallel to said bottom floor and the volume below said annular crest and above said bottom floor being a concentrated sample well;

a membrane support member held below said bottom of said sample reservoir, said membrane support including a membrane support web comprising a plurality of spokes with open spaces between the spokes, said membrane support positioned below said central opening in the bottom of said sample reservoir;

a circular membrane held on said membrane support web, said membrane held in a leak proof manner by membrane sealing means so that any liquid on the top of said membrane cannot pass around said membrane;

a generally cylindrical filtrate vial having an open top, a closed, generally conical bottom, said filtrate vial being ventingly held by said membrane support member and positioned below said membrane so that filtrate passing through said membrane will be collected in said filtrate vial; and a retentate vial ventingly held over the open top of said sample reservoir whereby a sample to be concentrated may be placed in said sample reservoir and covered by said retentate vial and placed in a centrifuge and spun so that the molecules in the sample which are smaller than the cutoff of the membrane will pass through the membrane but a small volume of concentrated sample will be held in the concentrated sample well after which the fitrate vial is removed and the remaining assembly may be inverted and spun again forcing the concentrated sample into the retentate vial.

6. The concentrator of claim 5 wherein the membrane support comprises three diametric arms which are equally spaced from one another.

7. The concentrator of claim 6 wherein the filtrate vial has exterior threads near the top thereof and further including a filtrate cap with internal threads which match with the threads on the filtrate vial.

* * * * *